United States Patent [19]
Wider

[11] Patent Number: 6,071,961
[45] Date of Patent: Jun. 6, 2000

[54] ANTIMICROBIAL COMPOSITION AND METHODS OF USE THEREFOR

[76] Inventor: Michael D. Wider, #8 Hanover, Pleasant Ridge, Mich. 48069

[21] Appl. No.: 09/077,148
[22] PCT Filed: Nov. 25, 1996
[86] PCT No.: PCT/US96/18899
§ 371 Date: Dec. 9, 1998
§ 102(e) Date: Dec. 9, 1998
[87] PCT Pub. No.: WO97/19593
PCT Pub. Date: Jun. 5, 1997

Related U.S. Application Data
[60] Provisional application No. 60/014,617, Nov. 28, 1995.
[51] Int. Cl.[7] .................................................. A61K 31/19
[52] U.S. Cl. .......................... 514/557; 514/558; 514/568; 514/574; 514/517
[58] Field of Search ..................... 514/557, 558, 514/568, 574, 517

[56] References Cited

U.S. PATENT DOCUMENTS

| | | | |
|---|---|---|---|
| 4,404,040 | 9/1983 | Wang | 134/22.14 |
| 4,975,217 | 12/1990 | Brown-Skrobot et al. | 252/107 |
| 5,208,257 | 5/1993 | Kabara | 514/552 |
| 5,280,042 | 1/1994 | Lopes | 514/557 |
| 5,460,833 | 10/1995 | Andrews et al. | 424/606 |

FOREIGN PATENT DOCUMENTS

| | | |
|---|---|---|
| 94/10837 | 5/1994 | WIPO . |
| 94/31956 | 11/1995 | WIPO . |

OTHER PUBLICATIONS

Jain et al, Pharmazie, 46, pp 798–800, 1991.

Walsh et al N. Eng. J Med 333(15) pp 984–991, Oct. 12, 1995.

*Primary Examiner*—Rebecca Cook
*Attorney, Agent, or Firm*—Plunkett & Cooney, P.C.

[57] ABSTRACT

A composition for arresting H. pylori bacterium in the body of an individual includes an antimicrobial agent, a hydrotrope and a hydrotrope compatible acid. The composition may be ingested orally. Thus, each of the components are food grade or is of sufficiently low toxicity to enable oral ingestion thereof.

13 Claims, No Drawings

ANTIMICROBIAL COMPOSITION AND METHODS OF USE THEREFOR

CROSS REFERENCE TO RELATED APPLICATION

This application is a 371 of PCT/US96/18899 filed Nov. 25, 1996 which claims priority to provisional patent application Ser. No. 60/014,617, filed Nov. 28, 1995 for "Antimicrobial Composition and Methods of Use Therefor", the disclosure of which is hereby incorporated by reference.

BACKGROUND OF THE INVENTION

1. Field of the Invention

The present invention pertains to antimicrobial compositions. Even more particularly the present invention concerns the use of antimicrobial compositions and the treatment of gastritis. Most particularly, the present invention concerns the use of food grade components in antimicrobial compositions for the treatment of gastritis.

2. Prior Art

It has been theorized that the gram negative bacterium *H. pylori*, previously referred to in the art as *campylobacter pyloridis*, is the cause of gastric and duodenal ulceration associated with chronic gastritis. Further, individuals infected with *H. pylori* have been observed to have an increased rate of gastric cancer. Therefore, a simple efficacious manner of eliminating this bacterium from the system would be more advantageous.

As is known, *H. pylori* is found at the epithelial cell junctions beneath the mucus layer of the stomach and is, therefore, thought to be effectively killed by systemic exposure to antibiotics as well as by direct luminal contact, thus, curing gastric and duodenal ulceration and decreasing the incidence of recurrence. Because of the observed and potential development of antibiotic resistant strains of *H. pylori* and the difficulty of penetrating the hydrophobic gastric mucus, coupled with the observed failure or ineffectiveness of single antibiotic therapy, the combination of 2 or 3 antibiotics is typically used.

Further, the administration of large doses of antibiotic exposes the patient to the risk of developing opportunistic infections with other antibiotics resistant organisms.

Yet, treatment other than with antibiotics for the elimination of *H. pylori* has not been readily perceived heretofore, because the elimination of *H. pylori* from the gastric mucosa is difficult for several reasons. First, it is difficult to prove that the bacteria is even present in the stomach. Therefore, it is equally difficult to monitor when it has been eliminated. Second, while *H. pylori* is normally killed by low pH, it has been observed to penetrate the mucus layer covering the gastric mucosa, which has a neutral pH. The gastric mucus acts as an unstirred layer and contains bicarbonate ions which buffer the layer, protecting the bacterium from the normal gastric, luminal pH of about 2 to about 4. Third, as noted above, a single antibiotic is frequently ineffective in eliminating *H. pylori* from the stomach.

As high as 10% of the population in the United States suffers from chronic inflammation of the stomach and duodenum in their lifetime. While nearly all patients with chronic gastritis have *H. pylori* infections, not all cases of *H. pylori* gastritis are associated with ulceration. Therefore, exposure of patients to the several and significant risks involved in triple antibiotic therapy is not warranted without sufficient testing to demonstrate the presence of *H. pylori* infection and associated ulceration.

As detailed hereinafter, the present invention provides a simple inexpensive way of treating *H. pylori*.

SUMMARY OF THE INVENTION

In a first aspect hereof and in accordance herewith there is provided a composition for arresting or eliminating *H. pylori* bacteria which, generally, comprises:

(a) an antimicrobial agent;

(b) a hydrotrope or solubilization agent or solubilizer;

(c) a hydrotrope compatible acid, and optionally, (d) a vehicle or transport medium for the composition.

In a critical aspect hereof, each of the components used in the composition are "food grade" or have sufficiently low toxicity levels to permit ingestion or otherwise is enabled to be introduced internally into the body of a user.

Preferably, the composition hereof has a pH ranging from about 1 to about 5.

In another facet hereof, there is provided a method for arresting or eliminating *H. pylori* bacteria from the body of the user which, generally, comprises contacting the *H. pylori* bacteria with the antimicrobial composition hereof. Contacting the bacterium with the composition is achieved by ingesting or otherwise introducing the composition into the digestive tract of the user.

The composition may be ingested either as a liquid, as a gelatinized capsule or may be introduced by any other suitable medium which permits the introduction of the composition into the body of the user.

For a more complete understanding of the present invention reference is made to the following detailed description and accompanying examples.

DESCRIPTION OF THE PREFERRED EMBODIMENT

At the outset, it is to be noted that the present invention relates to the use of sanitizing and disinfecting compositions of matter to eliminate infestations of the gastrointestinal tract by microorganisms. As known, these infestations range from colonic infections with pathogenic microorganisms including bacteria, yeast, fungi, rickettsia and the like to intestinal and gastric overgrowth with pathogenic and non-pathogenic microorganisms. The invention is particularly directed to the treatment of gastritis and related ulceration of the stomach and duodenum caused by bacterium *Helicobacter pylori* (hereinafter *H. pylori*).

The use of food grade compositions of matter or disinfectant active agents with low toxicity will essentially eliminate the risk associated with antibiotic treatment, allowing prophylactic treatment.

Thus, and in accordance herewith there is provided an antimicrobial composition for the elimination of *H. pylori* which, generally, comprises:

(a) an antimicrobial agent;

(b) a hydrotrope or solubilization agent or solubilizer;

(c) a hydrotrope compatible acid, and optionally, (d) a vehicle or transport medium for the composition, wherein the components are "food grade" or have low toxicity levels to permit ingestion or can otherwise can be introduced internally into the body of the user.

The composition hereof has a pH ranging from about 1 to about 5 and, preferably ranges from about 2.5 to about 3.5.

The composition hereof can be prepared as a concentrate which can, then, be diluted with water or other diluent for usage. Alternatively, the composition can be prepared directly as a use composition such as in a gelatinized capsule, as a tablet, etc.

The Antimicrobial Active Agent

The antimicrobial active agent contemplated for use herein is, preferably, a food grade, aliphatic or aromatic fatty acid, either saturated or unsaturated, preferably, saturated, and having from about 6 to about 20 carbon atoms and, preferably, from about 8 to about 12 carbon atoms, as well as mixtures thereof.

The fatty acid may be linear, branched or cyclic and may contain substituent atoms such as hydroxyl groups or ether linkages as long as the substituents do not affect antimicrobial activity. Preferably, the fatty acids employed is food grade, linear, saturated and unsubstituted. Representative of the fatty acids contemplated for use herein include caproic acid, caprylic acid, capric acid and lauric acid, as well as mixtures thereof.

A particularly preferred fatty acid is caprylic acid.

The Solubilizer

The hydrotrope or solubilizing agent or solubilizer is employed to enhance the stability or antimicrobial activity or penetration of the mucosal layer by the fatty acid.

The antimicrobial action of short chain fatty acids is significantly greater in the protonated state. However, undissociated fatty acids have negligible solubility in water. Thus, the solubilizer brings the fatty acid(s) into aqueous solution, either when diluted into the use solution or by the gastric juices.

Hydroptropes or solubilizers for fatty acids are well known in the art. The preferred solubilizer is non-toxic and retains fatty acids in aqueous solution in the use solution.

Preferred solubilizers for use herein include anionic surfactants such as alkylphosphates or phosphonates, sugar esters, alkyl glycosides, alkyl sulfates, alkane sulfonates, alpha olefin sulfonates, linear alkyl benzene or napthalene sulfonates, secondary alkane sulfonates, alkyl ether sulfates or sulfonates and diaklylsulfosuccinic acid esters as well as mixtures thereof. The preferred solubilizer for use herein is food grade, sodium lauryl sulfate.

It is believed that the solubilizer, besides hydrotroping the fatty acids into solution, also, disrupts the gastric mucus allowing exposure of infecting organisms to the disinfectant in the lumen of the stomach or intestines, since the gastric mucus is known to be hydrophobic and to be disrupted by solubilizing agents such as hydrotropes and surfactants.

Hydrotrope Compatible Acid

The disinfectant composition requires the presence of a hydrotrope compatible acid in sufficient concentration to provide a pH in the range of about 1 to about 5, and preferably from about 2.5 to about 3.5, when the use composition is diluted by gastric secretions. The selected acid should be compatible with product stability and not cause the chemical degradation of the hydrotrope. The acid is, generally, a weak, food grade, organic acid such as but not limited to citric acid, acetic acid, fumaric acid and maleic acid and the like as well as mixtures thereof. Mineral acids will produce the same effect but are more difficult to formulate in an ingestible form. Organic acids are generally preferred, especially when sulfated or sulfonated hydrotropes are used due to their instability in mineral acids. Food grade, citric acid is preferred. Citric acid provides added antimicrobial effects since citric acid is known in the art to be biocidal.

Vehicle

The preferred vehicle, where used, is water. However, it is not essential hereto.

The disinfectant composition of the present invention can be formulated in a concentrate without the addition of water or other optional agents.

Also, depending on the end use of the present invention the composition may include flavoring agents, gums, colorants, sweeteners or salts as approved for use in medications and foods by the United States Food and Drug Administration in the Code of Federal Regulations.

In preparing the composition hereof, generally, it is prepared as a liquid concentrate by admixing the components together at ambient temperature. Generally, the concentrate will comprise from about 0.1% to about 15% by weight of the fatty acid based on the total weight, from about 0.1% to about 30%, by weight of the hydrotrope based on the total weight, from about 0.1% to about 50% by weight of the hydrotrope compatible acid based on the total weight, the balance being the vehicle as well as any other components.

In preparing a use solution the composition is diluted with water or other suitable fluid in which the concentrate is stable. Preferably the diluent is water. Typically, the use solution will contain, by weight, from about 0.1% to about 10% of concentrate, with the balance being diluent.

For a more complete understanding of the present invention, reference is made to the following illustrative, non-limiting examples in which all parts are by weight, absent contrary indications.

EXAMPLE I

This example illustrates the preparation of an antimicrobial composition in accordance herewith.

Into a suitable vessel equipped with stirring, was added at ambient conditions, the following:

| Ingredient | amt, pbw |
| --- | --- |
| caprylic acid | 0.5 |
| sodium lauryl sulfate | 0.5 |
| citric acid | 0.5 |
| water | 98.5 |

The concentrate has a pH of about 3.3 and is a water white liquid. The concentrate is, then, diluted with water in a 1:20 weight ratio to provide the use composition. The resulting composition has a pH of about 3.5.

EXAMPLE II

This example illustrates the utilization of the antimicrobial composition of the present invention.

The composition of Example I is orally administered by admixing 5 parts (by volume) of the composition of Example I with approximately 100 parts of cold tap water to provide a "dose" thereof. This dose is taken three times per day. The first dose is taken following an approximate ten hour fast and at least 30 minutes prior to ingesting any food or drink. Subsequent doses are taken approximate 30 minutes before meals.

The final dosage form of the composition is a 0.25 part antimicrobial fatty acid, a 0.25 part surfactant and 0.25 part acid, based on a 5 part dose.

The present invention is contemplated as either a concentrated solution for dilution into a suitable vehicle for oral administration or a ready to use solution. However, it may be encapsulated or incorporated into other solid forms such as a gel, a time release capsule and the like known in the medicinal arts.

It is readily perceived by one skilled in the art that the major difficulty in the treatment of *H. pylori* infections is overcome hereby, i.e., penetration of the gastric mucus, which is achieved by the active agents. Even the neutral pH of the mucus is overcome by the present invention.

The disinfectant compositions of the present invention meet the need for elimination of pathogenic organisms from the gastrointestinal tract of animals and human by direct, luminal contact with bactericidal and fungicidal agents, avoiding the use of antibiotics. Further, since the disinfectant and sanitizing compositions hereof employ only food grade compositions of matter, concerns over potential toxicity is eliminated. The present invention allows prophylactic treatment of patients presenting with chronic gastritis prior to the development of gastric or duodenal ulcers without expensive and frequently invasive testing due to the absence of risk in relation to toxicity.

Those skilled in the art will recognize that there are many sanitizing and disinfecting compositions which employ a variety of substances as the active agent including, but not limited to, quaternary ammonium compounds, fatty acids, anionic surfactants, organic acids, halogens and sulfated and sulfonated aliphatic acids, other than those enumerated above. Theoretically any such antimicrobial compound may be used herein. However, depending on the toxicity levels of these compounds their applicability hereto may be diminished. But it is to be understood, that so long as the toxicity level is low enough such compounds are within the scope hereof.

Thus, in its broadest aspect the present invention provides for the arresting of *H. pylori* bacteria by the contacting thereof with an antimicrobial compound at levels safe for ingestion.

Having, thus, described the invention what is claimed is:

1. A method for arresting *H. pylori* bacterium in the body of an individual in need thereof comprising:
   ingesting an *H. pylori* arresting amount of a composition comprising
   (a) an *H pylori* arresting antimicrobial agent selected from the group consisting of an aliphatic fatty acid and an aromatic fatty acid or a mixture thereof, the fatty acid having from about 6 to about 20 carbon atoms, the acid being either saturated or unsaturated;
   (b) a hydrotrope;
   (c) a hydrotrope compatible acid.

2. The method of claim 1 wherein the composition has a pH ranging from about 1 to about 5.

3. The method of claim 2 wherein the pH of the composition ranges from about 2.5 to about 3.5.

4. The method of claim 1 wherein the composition further comprises: [a] an orally ingestible transport medium for the composition.

5. The method of claim 4 in which the transport medium for the composition is water.

6. The method of claim 1 wherein in the composition the fatty acid is a linear unsubstituted saturated fatty acid.

7. The method of claim 6 wherein in the composition the fatty acid is selected from the group consisting of caproic acid, caprylic acid, capric acid and lauric acid or mixtures thereof.

8. The method of claim 1 wherein in the composition the hydrotrope is an anionic surfactant.

9. The method of claim 8 wherein in the composition the anionic surfactant is selected from the group consisting of alkylphosphates or phosphonates, sugar esters, alkyl glycosides, alkyl sulfates, alkane sulfonates, alpha olefin sulfonates, linear alkyl benzene or napthalene sulfonates, secondary alkane sulfonates, alkyl ether sulfates or sulfonates and diaklylsulfosuccinic acid esters or mixtures thereof.

10. The method composition of claim 9 wherein in the composition the anionic surfactant is sodium lauryl sulfate.

11. The method composition of claim 1 wherein in the composition the hydrotrope compatible acid is selected from the group consisting of citric acid, acetic acid, fumaric acid and maleic acid or mixtures thereof.

12. The method of claim 4, wherein in the composition
   (a) the antimicrobial compound comprises from about 0.1% to about 15%, by weight, based on the total weight;
   (b) the hydrotrope comprises from about 0.1% to about 30%, by weight, based on the total weight;
   (c) the hydrotrope compatible acid comprises from about 0.1% to about 50%, by weight, based on the total weight; and
   (d) the balance is a transport medium vehicle for the composition.

13. A method for arresting *H. pylori* bacterium in the body of an individual in need thereof comprising:
   ingesting an *H. pylori* arresting amount of an antimicrobial agent selected from the group consisting of an aliphatic fatty acid and an aromatic fatty acid or a mixture thereof, the fatty acid having from about 6 to about 20 carbon atoms, the acid being either saturated or unsaturated.

* * * * *